(12) United States Patent
Yamada et al.

(10) Patent No.: US 9,586,254 B2
(45) Date of Patent: Mar. 7, 2017

(54) WIRE SAW

(71) Applicant: TOKYO WIRE WORKS, LTD., Tokyo (JP)

(72) Inventors: Hiroyoshi Yamada, Tokyo (JP); Kazunari Mochizuki, Tokyo (JP); Satoshi Shimura, Iwate (JP)

(73) Assignee: TOKYO WIRE WORKS, LTD., Tokyo (JP)

(*) Notice: Subject to any disclaimer, the term of this patent is extended or adjusted under 35 U.S.C. 154(b) by 327 days.

(21) Appl. No.: 14/342,423

(22) PCT Filed: Oct. 17, 2012

(86) PCT No.: PCT/JP2012/076766
§ 371 (c)(1),
(2) Date: Mar. 3, 2014

(87) PCT Pub. No.: WO2013/179509
PCT Pub. Date: Dec. 5, 2013

(65) Prior Publication Data
US 2014/0222004 A1    Aug. 7, 2014

(30) Foreign Application Priority Data

May 29, 2012   (WO) .................. PCT/JP2012/063741
Sep. 5, 2012   (JP) ................................ 2012-195423

(51) Int. Cl.
*A61B 17/14*    (2006.01)
*B21F 45/00*    (2006.01)
(Continued)

(52) U.S. Cl.
CPC ............ *B21F 45/008* (2013.01); *A01K 17/00* (2013.01); *A61B 17/149* (2016.11); *B23D 61/185* (2013.01); *Y10T 83/9292* (2015.04)

(58) Field of Classification Search
CPC ................ B28D 5/045; B24B 27/0633; A61B 2017/32006; A61B 2017/320064;
(Continued)

(56) References Cited

U.S. PATENT DOCUMENTS 184,804 A * 11/1876 Stohlmann ............. A61B 17/14
                                                        125/21
626,621 A *  6/1899 L'Hoir et al. ....... B23D 61/185
                                                        125/12
(Continued)

FOREIGN PATENT DOCUMENTS

DE       1427778        1/1969
FR        364924     *  4/1906
(Continued)

*Primary Examiner* — David Bates
(74) *Attorney, Agent, or Firm* — Michael Tobias

(57) ABSTRACT

A wire saw which has excellent cutting ability and which is not easily clogged by chips formed by cutting is provided. It has a body 6 having a first metal wire 1 which is made of a cobalt-based alloy, two second metal wires 2a and 2b which are made of a cobalt-based alloy, and three third metal wires 3a-3c which are made of a cobalt-based alloy and are wound on the first metal wire 1. The second metal wires 2a and 2b are helically wound on each of the third metal wires 3a-3c in opposite directions so as to cross each other. Cutting teeth are constituted by projections 8 which are formed by the crossing points of the two second metal wires 2a and 2b.

16 Claims, 4 Drawing Sheets

(51) Int. Cl.
*A01K 17/00* (2006.01)
*B23D 61/18* (2006.01)

(58) Field of Classification Search
CPC ........ A61B 2017/143; A61B 2017/145; A61B 17/148; B23D 61/185
USPC .......... 606/177; 451/535; 125/16.02, 21, 38; 83/651.1
See application file for complete search history.

(56) References Cited

U.S. PATENT DOCUMENTS

| | | | | |
|---|---|---|---|---|
| 640,139 | A * | 12/1899 | L'Hoir et al. ....... | B23D 61/185 125/12 |
| 1,306,636 | A * | 6/1919 | Selby ................... | B23D 61/185 125/12 |
| 1,687,089 | A * | 10/1928 | Green .................. | B23D 61/185 125/18 |
| 1,730,756 | A * | 10/1929 | Brown ................. | B23D 61/185 125/12 |
| 2,083,369 | A * | 6/1937 | Greene ................ | B23D 61/185 125/21 |
| 2,451,383 | A * | 10/1948 | Avaucourt ........... | B23D 61/185 125/12 |
| 2,714,790 | A * | 8/1955 | Lindenborg ......... | B23D 61/185 125/21 |
| 2,773,495 | A * | 12/1956 | Lefevre ............... | B23D 61/185 125/21 |
| 3,150,470 | A * | 9/1964 | Barron ................ | B23D 61/185 125/21 |
| 3,495,590 | A * | 2/1970 | Zeiller .................... | A61F 15/02 30/166.3 |
| 4,015,931 | A * | 4/1977 | Thakur ................ | B23D 61/185 125/21 |
| 4,033,213 | A | 7/1977 | Eiselt et al. ....................... | 83/56 |
| 4,164,162 | A * | 8/1979 | Eiselt .................... | B23D 61/185 125/12 |
| 4,464,836 | A * | 8/1984 | Hissa ..................... | B23D 51/14 16/442 |
| 4,464,892 | A * | 8/1984 | Kleijwegt ............. | D07B 1/062 152/451 |
| 4,580,545 | A * | 4/1986 | Dorsten ................ | B23D 65/00 125/21 |
| 4,709,699 | A * | 12/1987 | Michael ................. | A61B 17/14 125/18 |
| 6,526,960 | B2 * | 3/2003 | Asada .................... | B23D 65/00 125/18 |
| 7,189,240 | B1 * | 3/2007 | Dekel .................... | A61B 17/14 606/84 |
| 8,137,353 | B2 * | 3/2012 | Tomita ................... | A61B 17/14 606/82 |
| 8,398,641 | B2 * | 3/2013 | Wallace ............... | A61B 17/025 606/79 |
| 9,314,253 | B2 * | 4/2016 | Mimran ............. | A61B 17/1671 |
| 2010/0175677 | A1 * | 7/2010 | Chiang ................ | B23D 61/185 125/39 |
| 2014/0114315 | A1 * | 4/2014 | Leguidleguid ......... | A61B 17/14 606/79 |

FOREIGN PATENT DOCUMENTS

| | | |
|---|---|---|
| JP | 50160382 | 12/1975 |
| JP | 61020701 | 1/1986 |
| JP | 09254006 | 9/1997 |
| JP | 2000271872 | 10/2000 |
| JP | 2002066901 | 3/2002 |
| JP | 2003334763 | 11/2003 |
| JP | 2004237376 | 8/2004 |
| JP | 2004338023 | 12/2004 |
| JP | 2008017953 | 1/2008 |
| JP | 2011230258 | 11/2011 |

* cited by examiner

WIRE SAW

TECHNICAL FIELD

This invention relates to a wire saw.

BACKGROUND ART

A wire saw is constituted by strands having indentations and projections corresponding to the cutting teeth of a saw formed on the surface of a wire. A wire saw cuts objects by reciprocating like a saw. Wire saws are widely used for medical treatment, on dairy farms, and in industry.

A wire saw for medical treatment is used to amputate a human limb. For example, at a site of emergency medical treatment where a building has collapsed due to an earthquake or where a vehicle accident has taken place, urgent rescue by rapidly amputating a limb of an injured person who is trapped by rubble or a vehicle is sometimes necessary. When it is not possible to transport sufficient equipment for medical treatment to the site, a physician uses a portable wire saw for amputating limbs. Such a wire saw for amputating limbs is manufactured and sold by Johnson & Johnson K.K. under the product name Gigli wire saw.

FIG. 5 depicts explanatory views of a wire saw 20 in the form of a Gigli wire saw. FIG. 5(a) shows the overall structure, FIG. 5(b) shows an enlargement of end portion 22 in FIG. 5(a), FIG. 5(c) shows an enlargement of end portion 23 in FIG. 5(a), and FIG. 5(d) is a partially enlarged view of the wire (saw portion) 21 in FIG. 5(a).

The wire saw 20 has a wire (saw portion) 21 which forms a body portion and end portions 22 and 23 which are formed at both ends of the wire 21. The wire 21 is constituted by two stainless steel core wires 21a and 21b which are twisted together in a helical manner and stainless steel fine wires 21c, 21c which are twisted around the core wires 21a and 21b, respectively. A large number of projections formed by the fine wires 21c and a large number of indentations formed between adjoining projections are continuously formed on the periphery of the core wires 21a and 21b. The projections act as cutting teeth. Chips formed by cutting are removed via the indentations. As shown in FIG. 5(a), the wire saw 20 is flexible and can be wound into a small shape.

Loop-shaped engaging portions 24 for engagement with a handle (not shown) held by a physician are provided at the end portions 22 and 23. At a site of emergency medical treatment, a physician unwinds the wire saw 20 which he is carrying in a small wound-up shape and extends it, he attaches the engaging portions 24, 24 to a handle, and after placing the wire saw 20 on the portion to be cut while holding the handle, he amputates a limb of an injured person by reciprocating the wire saw 20 in its lengthwise direction.

A wire saw for dairy farms is used when cutting off the horns of livestock in order to prevent accidents due to goring of cattle or other livestock. Nerves pass through cattle horns, so when a cattle horn is cut off with a wire saw, the effect is obtained that bleeding is stopped by the heat of friction.

An industrial wire saw is used when cutting silicon wafers for semiconductors, for example. A wire saw has finer cutting teeth compared to a rotating disc-shaped cutter, so it is possible to perform cutting with a smaller kerf width.

It is known that the cutting ability of a wire saw can be improved by adhering abrasive particles, diamonds, or the like, to the surface of a wire (see Patent Documents 1-6).

Patent Document 7 discloses a wire saw comprising at least two strands which are made of carbon fibers and are twisted together. The cross-sectional shape of at least one strand is a polygon or an ellipse.

Patent Document 8 discloses a wire saw for bone cutting having a central core strand and a braided layer comprising metal strands provided on its periphery as an outer peripheral surface.

Patent Document 9 discloses a structure in which a winding is provided atop another winding. This structure is for use in cutting plastic, and this document only discloses using a curved surface constituted by a single winding as a cutting blade.

Patent Documents 10-13 are documents showing the level of the prior art.

Patent Document 10 discloses a two-strand structure. One strand is formed, and then it is twisted together with another wire to form a larger strand.

Patent Document 11 discloses a structure in which an outer peripheral surface has a braided structure, and a coating layer of diamond grinding particles is provided on one strand of the braided structure.

Patent Document 12 discloses a structure in which a layer of grinding powder is provided on strands forming an outer peripheral surface.

Patent Document 13 discloses an abrasive rope with a strand structure having an abrasive tape material provided on its surface.

PRIOR ART DOCUMENTS

Patent Documents

Patent Document 1: JP 2000-271872 A
Patent Document 2: JP 2002-66901 A
Patent Document 3: JP 2003-334763 A
Patent Document 4: JP 2004-237376 A
Patent Document 5: JP 2011-230258 A
Patent Document 6: JP 2004-338023 A
Patent Document 7: JP H9-254006 A
Patent Document 8: JP 2008-17953 A
Patent Document 9: JP S50-160382 A
Patent Document 10: JP S61-20701 A
Patent Document 11: US 2010/0175677 A1
Patent Document 12: DE 1427778
Patent Document 13: U.S. Pat. No. 2,714,790

SUMMARY OF THE INVENTION

Problem which the Invention is to Solve

Each of the above-described types of wire saw does not have sufficient cutting ability. In particular, because they do not have sufficient cutting ability when a physician is reciprocating the wire saw by hand, it takes a long time to amputate a limb of an injured person at a site of emergency medical treatment.

Although a conventional wire saw has excellent cutting ability immediately after the start of cutting, it quickly becomes clogged by chips formed by cutting, and excellent cutting ability cannot be maintained over a long period. This is one reason why it takes a long time to amputate a limb of an injured person.

An improvement in cutting ability and an increase in the ability to remove chips formed by cutting is desired not only for wire saws for medical treatment but also for wire saws for dairy farms and industrial wire saws.

Means for Solving the Problem

As shown by below-described FIGS. 1-3, the present invention is a wire saw 7 having a body 6 constituted by a first metal wire 1, at least one third metal wire 3a, 3b and 3c which is twisted around the first metal wire 1, and at least two second metal wires 2a and 2b which are twisted in opposite directions around the third metal wire. The two second metal wires 2a and 2b are helically twisted in opposite directions from each other on the third metal wire in a state in which they cross each other preferably with a constant pitch, and then the third metal wire is twisted around the periphery of the first metal wire 1.

Namely, the present invention is wire saw having a body having a first metal wire, at least two second metal wires, and at least one third metal wire, characterized in that the two second metal wires are helically twisted around the periphery of the third metal wire in opposite directions so as to cross each other, and the third metal wire is wound around the outer periphery of the first metal wire.

As a result, the projections 8 and indentations 9 formed by the crossing points of the two second metal wires 2a and 2b in the wire saw 7 (see FIG. 2) are continuously and alternatingly formed in the lengthwise direction of the third metal wire and accordingly in the lengthwise direction of the first metal wire. Such an arrangement of indentations and projections and particularly the alignment of the projections corresponds to the cutting teeth of the saw.

The body 6 of the wire saw 7 preferably has three third metal wires 3a, 3b, and 3c which are wound in the same direction on the first metal wire 1, and as described above, the two second metal wires 2a and 2b are twisted in opposite directions from each other around each of the third metal wires 3a-3c.

From another standpoint, the present invention is a method of manufacturing a wire saw characterized by having the below-described first step, second step, and third step.

First step: One second metal wire 2a of at least two second metal wires 2a and 2b is twisted around the third metal wire 3a preferably with a constant pitch to manufacture a two-strand wire 4.

Second step: The other second metal wire 2b of the two second metal wires 2a and 2b is twisted around each of the third metal wires 3a, 3b, and 3c in the opposite direction from the direction of twist of the two-strand wire 4 with the same pitch as or a different pitch from second metal wire 2a to manufacture a three-strand wire 5 in which the metal wires 2a and 2b cross each other. One or more (preferably 3) of these three-strand wires 5 is manufactured.

Third step: One or more of the three-strand wires 5 is wound around the first metal wire 1 to manufacture a wire saw body 6.

A wire saw body 6 which is manufactured in this manner is cut to a suitable length to make a wire saw 7. In order to make a wire saw for amputating limbs which can be carried by a physician, an engaging portion (not shown) for engaging a handle on which the wire saw body is mounted at the time of use is formed at both ends of the wire saw body 6 to form a wire saw 7. In the present invention, there are no particular limitations on the shape of the engaging portion for a handle or on its method of manufacture. A conventional method can be used.

In this description, for convenience, the first, second, and third wires are referred to as a first metal wire, a second metal wire, and a third metal wire. However, any type of wire can be used as long as it can form cutting teeth. Depending upon the application, it is also possible to use inorganic wires made of carbon fibers, ceramic fibers, or the like.

Effects of the Invention

Because a wire saw according to the present invention has the properties that it is light weight, compact, and flexible, it has excellent portability. A wire saw according to the present invention has superior cutting ability to a conventional wire saw. In addition, a wire saw according to the present invention does not readily become clogged by chips formed by cutting, so it can maintain an excellent cutting ability for long periods.

BRIEF EXPLANATION OF THE DRAWINGS

FIG. 2 is an explanatory view showing the state when a three-strand wire is manufactured by twisting another second metal wire 2 around the two-strand wire in the opposite direction from the previously twisted second metal wire 2a preferably with the same pitch so as to cross second metal wire 2a.

FIG. 3(a) shows one third metal wire, and 3b shows all three of the third metal wires.

FIG. 5(a) shows the overall structure, FIG. 5(b) is an enlarged view of an end portion in FIG. 5(a), FIG. 5(c) shows an enlargement of another end portion in FIG. 5(a), and Figure (d) shows the wire (saw portion) of Figure (a).

MODES FOR CARRYING OUT THE INVENTION

1. Information A-E which is the Basis for Completing the Present Invention

As explained while referring to FIGS. 5(a)-5(d), the projections formed on a wire saw 20 function as the cutting teeth of a saw, and the indentations serve to remove chips produced by cutting. As a result of diligent investigations aimed at improving the cutting ability of a wire saw and its ability to remove chips formed by cutting, the present inventors obtained the following new information A-E and completed the present invention.

(A) By twisting at least two second metal wires on a third metal wire in a helical pattern in opposite directions from each other so that the two second metal wires cross preferably with the same pitch, a large number of projections formed by the crossing points of the two second metal wires function as cutting teeth. As a result, the cutting ability of the wire saw is improved compared to a conventional wire saw.

(B) By winding at least one third metal wire on which the two second metal wires are twisted on a first metal wire, the height of the large number of projections which are formed by the crossing points of the two second metal wires and the depth of the indentations formed between these crossing points are increased. As a result, adequate space for removing chips formed by cutting is provided, and excellent ability to remove chips formed by cutting is guaranteed.

(C) By making the number of third metal wires around which the two second metal wires are twisted a plurality such as three, the density of the projections and indentations per unit length of a wire saw can be further increased. As a result, the cutting ability and ability to remove chips formed by cutting are further increased.

Figure 1:
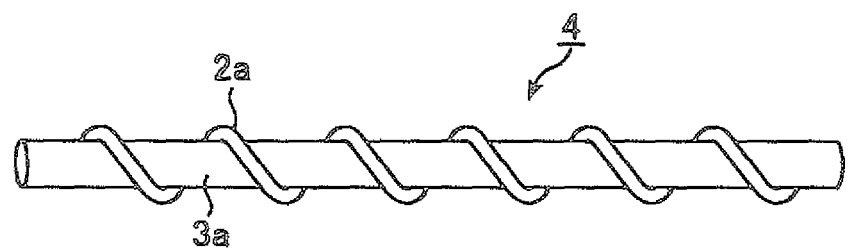
FIG. 1 is an explanatory view showing the state when a two-strand wire corresponding to cutting teeth of a saw is manufactured by combining a third metal wire and one second metal wire.

FIG. 1 is an explanatory view showing the state in which a two-strand wire 4 is manufactured by winding, namely by twisting, one second metal wire 2a around a third metal wire 3a.

Figure 2:
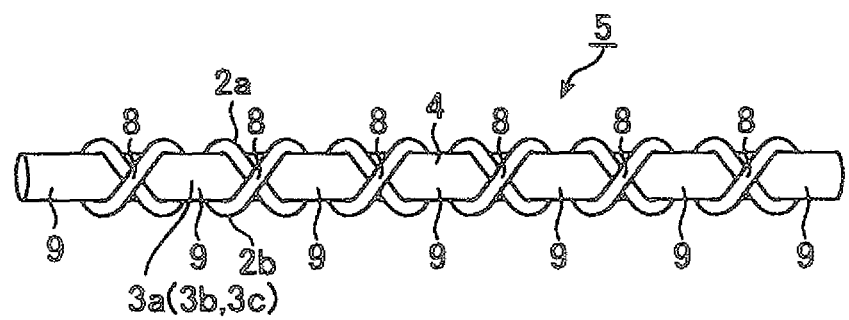

FIG. 2 is an explanatory view showing the state in which a three-strand wire 5 is manufactured by twisting one more second metal wire 2(b) on the two-strand wire 4 in the opposite direction from the previously twisted second metal wire 2a, preferably with the same pitch, so as to cross second metal wire 2a.

Figure 3:
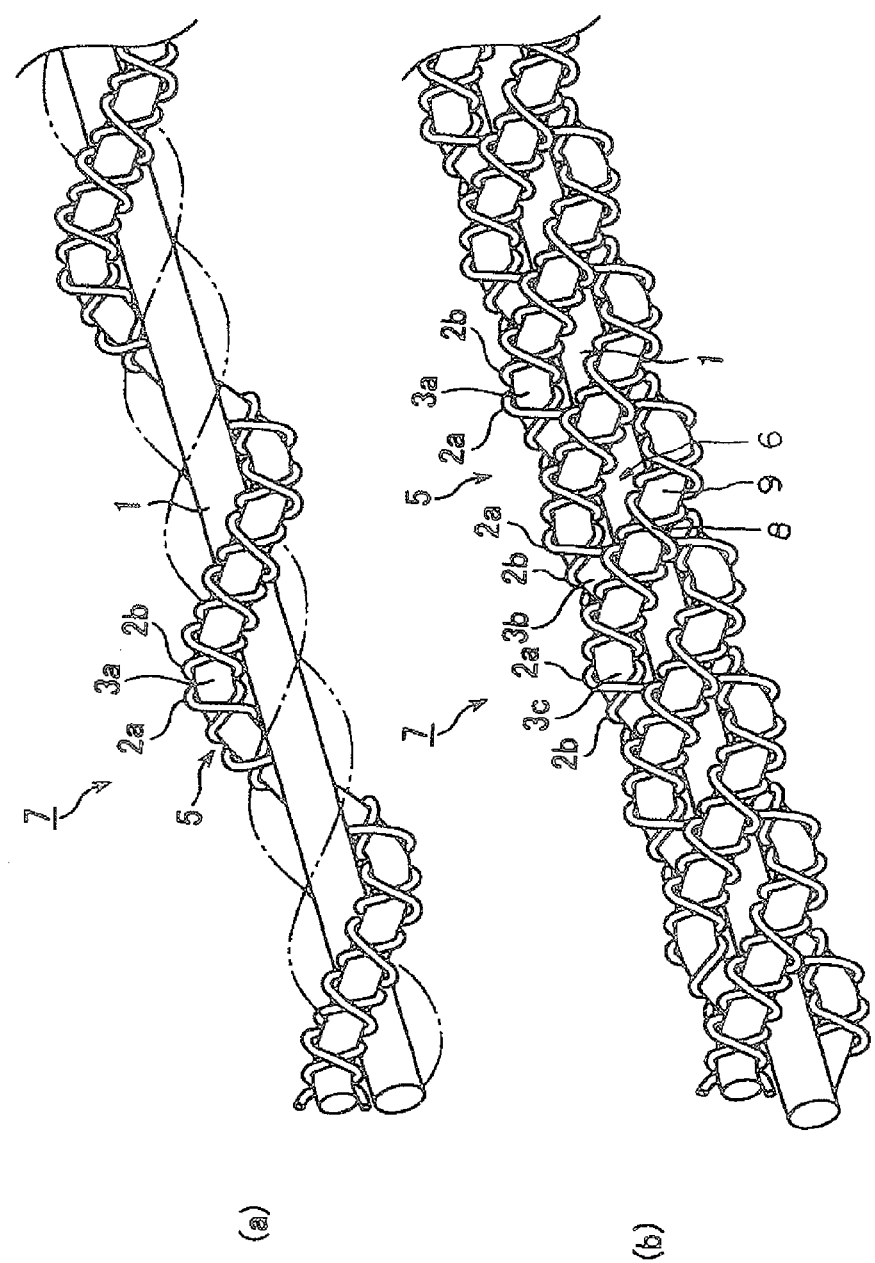
FIG. 3 comprises perspective views schematically showing the structure of a wire saw according to the present invention.

FIG. 3 comprises perspective views schematically showing the structure of a wire saw 7 according to the present invention. FIG. 3(a) shows only one third metal wire 3a, and FIG. 3(b) shows all three of the third metal wires 3a-3c.

As shown in FIG. 1, a two-strand wire 4 is manufactured by twisting together a third metal wire 3a and one second metal wire 2a.

As shown in FIG. 2, a three-strand wire 5 is manufactured by winding one more second metal wire 2b on the two-strand wire 4 in the opposite direction from the previously wound second metal wire 2a, preferably with the same pitch, so as to cross second metal wire 2a. The second metal wires 2a and 2b cross on the outer peripheral surface of the third metal wire 3a, and the crossing portions, namely, the projections constitute cutting teeth. The winding pitch of the second metal wires 2a and 2b which are twisted in opposite directions can be arbitrarily selected. However, if both metal wires 2a and 2b are wound with the same pitch, the projections formed by their crossing points, namely, the cutting teeth, can be regularly arranged in a straight line in the lengthwise direction of the third metal wire 3a.

As shown in FIGS. 3(a) and 3(b), a wire saw 7 (more precisely, a wire saw body 6, but for convenience, it will be referred to as a wire saw 7) is formed by winding on the circumference of a first metal wire 1 one or a plurality of three-strand wires 5 (in this explanation an example will be given of the case in which there are three) each constituted by a metal wire 3a, 3b, or 3c having two second metal wires 2a and 2b twisted thereon.

The two second metal wires 2a and 2b which cross on the circumference of the three third metal wires 3a, 3b, and 3c form cutting teeth having a large number of projections 8 and indentations 9. As a result, the wire saw 7 has superior cutting ability and superior ability to remove chips formed by cutting compared to a conventional wire saw.

The cutting ability is further improved when a large number of projections are regularly arranged in a straight line in the lengthwise direction of the wire saw as described above.

(D) The effects described above in A-C can be more stably obtained by having a structure in which the diameter and breaking load of the metal wires successively increase from the two second metal wires 2a and 2b to the at least one third metal wire 3a to the first metal wire 1.

If the wire saw develops elongation due to plastic deformation at the time of use (referred to below simply as elongation), the height of the large number of projections 8 and the depth of the large number of indentations 9 formed at the crossing points of the two second metal wires 2a and 2b, namely, the size and position of the spaces for removing chips formed by cutting vary, so there is a possibility of a decrease in the cutting ability and the ability to remove chips formed by cutting. However, because the three-strand wire 5 of the wire saw 7 is helically wound around the first metal wire 1, the crossing points of the second metal wires 2a and 2b, namely, the cutting teeth are secured to the third metal wire 3a with greater certainty. Therefore, elongation of the first metal wire 1 due to back and forth movement of the wire 7 can be entirely prevented, there is no deviation of the position of the cutting teeth, and as a result, a good cutting ability and good ability to remove chips forms by cutting can be maintained over long periods.

(E) By providing an engaging portion such as a ring or a hook at both ends of the first metal wire 1 which forms the body 6 of the wire saw 7 for engaging a handle (not shown) which is held by hand at the time of use of the body 6 of the wire saw 7, a physician can operate the wire saw in the same manner as a conventional wire saw.

2. Explanation of Embodiments

A wire saw 7 according to the present invention can be used for medical treatment, on dairy farms, or in industry. In the following explanation, an example will be given of the case in which the wire saw 7 is used for medical treatment where there is a strong demand for improvements in cutting ability and an increase in the ability to remove chips formed by cutting.

(1) Wire Saw 7

As shown in FIGS. 3(a) and 3(b), the wire saw 7 is constituted by at least one third metal wire 3a, 3b, and 3c around which at least two second metal wires 2a and 2b are wound in opposite directions and a first metal wire 1 on which the third metal wire is wound. An engaging portion (not shown) may be provided on both ends of the body 6 for manual operation. Of course, the wire saw may be automated for industrial use.

These features will be sequentially explained.

First Metal Wire 1:

The first metal wire 1 bears the mechanical strength of the wire saw 7 itself. The first metal wire 1 is a wire made of a metal such as a cobalt-based alloy (such as 19-21 mass percent of Cr, 14-16 mass percent of W, 9-11 mass percent of Ni, and a remainder of Co and impurities) or stainless steel (such as SUS316L austenitic stainless steel), or piano wire. A cobalt-based alloy has a high mechanical strength and excellent wear resistance.

Second Metal Wires 2a and 2b:

The second metal wires 2a and 2b serve as cutting teeth. There are at least two second metal wires 2a and 2b, such as two or three. The second metal wires 2a and 2b are made of metal, and they are preferably made of the above-described cobalt-based alloy, stainless steel, or piano wire.

A cobalt-based alloy has the properties that it has much lower adhesion of human fats and blood proteins compared to stainless steel, and that it is harder. Therefore, a wire saw having a metal wire made from a cobalt-based alloy can maintain a good cutting ability for long periods.

The at least two second metal wires 2a and 2b are helically wound around the below-described third metal wire in opposite directions so as to cross each other preferably with a constant pitch. The period (pitch) of helical winding of the second metal wires 2a and 2b is preferably around 4.0-8.0 mm in the lengthwise direction of the third metal wire 3a-3c in order to obtain good cutting ability. The third metal wire is wound in the transverse direction around the first metal wire, so the period (pitch) of winding of the second metal wires in the lengthwise direction of the first metal wire 1 becomes around 0.8-1.2 mm.

The period of winding of the second metal wires 2a and 2b corresponds to the pitch in the lengthwise direction of the crossing points of the metal wires, namely, of the cutting teeth. At first glance, the cutting teeth appear to be randomly disposed on the outer surface of the first metal wire, but by making the winding pitch of the second metal wires and the winding pitch of the third metal wire constant, the cutting teeth on the outer surface of the first metal wire 1 have a certain regularity, and they are disposed in a number of straight rows in the lengthwise direction of the first metal wire. By arranging the cutting teeth so as to form straight rows in this manner, the cutting ability and the ability to remove chips formed by cutting are further increased.

By combining the second metal wires 2a and 2b so that they cross in a helical manner in opposite directions from each other, the second metal wires 2a and 2b which form cutting teeth are secured on the surface of the third metal wire with certainty. Therefore, the occurrence of elongation of the first metal wire 1 due to reciprocating movement of the wire saw 7 can be entirely prevented, and as a result, good cutting ability and good ability to remove chips formed by cutting can be maintained for long periods.

As stated above, by twisting together the second metal wires 2a and 2b preferably with the same pitch, the projections 8 and indentations 9 formed by the crossing points of the second metal wires 2a and 2b are formed with a constant pitch. As a result, the excellent effect of the present invention that the cutting ability of the wire saw 7 and its ability to remove chips formed by cutting can be maintained constant regardless of the position in the lengthwise direction of the wire saw 7 is obtained. This effect was not known at all in the past.

The second metal wires 2a and 2b are preferably wound in close contact with the periphery of the third metal wires 3a-3c.

The projections 8 and indentations 9 which extend in the lengthwise direction of the two second metal wires 2a and 2b are formed by the crossing points 8 of the two second metal wires 2a and 2b.

The projections 8 are the crossing points of the second metal wires 2a and 2b and constitute the cutting teeth of the wire saw 7. The crossing points are at the locations of the maximum diameter of the wire saw 7. Together with the outer peripheral surface of the first metal wire, the indentations 9 which adjoin the projections 8 constitute portions of the wire saw 7 for removing chips formed by cutting. Therefore, even if the third metal wires 3a-3c are densely wound, an adequate space can be guaranteed.

Third Metal Wires 3a-3c:

The third metal wires 3a-3c serve to hold the second metal wires 2a-2b which constitute the cutting teeth and to position and secure the cutting teeth on the periphery of the first metal wire 1.

As stated above, the third metal wires 3a-3c also have the function of adequately guaranteeing space for removal of chips formed by cutting. By providing the third metal wires 3a-3c, a wire saw according to the present invention can suppress clogging by chips formed by cutting and maintain a good cutting ability for long periods.

The third metal wires 3a-3c are made of metal and are preferably made of the above-described cobalt-based alloy, stainless steel, or piano wire.

The third metal wires 3a-3c are wound on the outer peripheral surface of the first metal wire 1 and mounted thereon by being helically twisted.

The helical period (pitch) of each of the third metal wires 31-3c is preferably around 4.0-7.0 mm in the lengthwise direction of the first metal wire 1 in order to obtain a good cutting ability. The three third metal wires 3a-3c are preferably staggered (spaced from each other) by around 1.5-3.5 mm in the lengthwise direction of the first metal wire 1.

There is preferably at least one third metal wire 3a-3c and most preferably there are two or three, for example. In this explanation, an example will be given of the case in which there are three third metal wires 3a-3c.

As stated above, the second metal wires 2a and 2b are helically twisted in opposite directions so as to cross each other preferably with a constant spacing around each of the third metal wires 3a-3c.

The diameter of the first metal wire 1 is preferably greater than the diameter of the second metal wires 2a and 2b, and the diameter of the third metal wires 3a-3c is preferably smaller than the diameter of the first metal wire 1 and larger than the diameter of the second metal wires 2a and 2b. When the wire saw 7 is for medical treatment, specifically it is preferable that the first metal wire 1 have a diameter of 0.36-0.56 mm, that the third metal wires 3a-3c have a diameter of 0.20-0.40 mm and that the second metal wires 2a and 2b have a diameter of 0.08-0.16 mm.

By making the breaking load of the first metal wire 1 larger than the breaking load of the third metal wires 3a-3c and making the breaking load of the third metal wires 3a-3c larger than the breaking load of the second metal wires 2a and 2b, at the time of cutting with the wire saw, the first metal wire 1, the second metal wires 2a and 2b, and the third metal wires 3a-3c can be secured in place with certainty.

By setting the diameters and the breaking loads of the first metal wire 1, the second metal wires 2a and 2b, and the third metal wires 3a-3c in this manner, the second metal wires 2a and 2b are secured with certainty on the periphery of the first metal wire 1 by the third metal wires 3a-3c.

When the wire saw 7 is used on a dairy farm, the first metal wire 1 preferably has a diameter of 0.40-0.60 mm, the third metal wires 3a-3c preferably have a diameter of 0.30-0.50 mm, and the second metal wires 2a and 2b preferably have a diameter of 0.12-0.20 mm.

When the wire saw 7 is used in industry, the first metal wire 1 preferably has a diameter of 0.13-0.33 mm, the third metal wires 3a-3c preferably have a diameter of 0.10-0.20 mm, and the second metal wires 2a and 2b preferably have a diameter of 0.04-0.08 mm.

Engaging Portions:

By providing engaging portions for holding the body 6 of the wire saw 7 during use on both ends of the first metal wire 1 which is the center line forming the body 6 of the wire saw 7, for example, engaging portions which can be hooked on a handle, the wire saw can be operated in the same manner as a conventional wire saw.

The engaging portions may be of any type. For example, they can be engaging portions like the engaging portions 24 shown in FIGS. 5(b) and 5(c). The engaging portions can be constituted by a loop made of a metal wire having the same diameter and made of the same material as the first metal wire 1, and they can be connected to both ends of the first metal wire 1 by suitable connecting means such as welding or the like.

A physician at the site of emergency medical treatment can rapidly amputate a limb of an injured person by unwinding and extending the wire saw 7 which he is carrying in a wound-up state, attaching a handle (not shown) to the two engaging portions, placing the wire saw 7 on a portion to be amputated while holding the handle, and reciprocating the wire saw 7 in its lengthwise direction.

The wire saw 7 has a compound strand structure in which two second metal wires 2a and 2b cross on the outer peripheral surface of each of third metal wires 3a-3c and the third metal wires 3a-3c are wound on the outer peripheral surface of a first metal wire 1. As a result, a large value is guaranteed for the height of the projections 8 and the depth of the indentations 9 which are formed at the crossing points 8 of the second metal wires 2a and 2b, and the density of cutting teeth is extremely high.

In addition, because the second metal wires 2a and 2b which constitute the cutting teeth are firmly secured by the first metal wire 1 and the third metal wires 3a-3c, there is no deviation in their position due to the reciprocating movement of the body 6 of the wire saw 7 at the time of cutting, and the wire saw 7 maintains good cutting ability and good ability to remove chips formed by cutting.

(2) Manufacturing Method

A method of manufacturing the wire saw 7 is not limited to a particular method, but the following is a preferred manufacturing method.

As shown in FIG. 1, one second metal wire 2a of at least two second metal wires 2a and 2b is helically twisted (wound) around the outer periphery of a third metal wire 3a preferably with a constant pitch to manufacture a two-strand wire 4 in which two strands in the form of a third and a second metal wire are twisted together.

At this time, the helical period (pitch) of the second metal wire 2a is preferably around 0.8-1.2 mm in the lengthwise direction of the third metal wire 3a in order to obtain a desired cutting ability.

Next, as shown in FIG. 2, the other second metal wire 2b of the two second metal wires 2a and 2b is twisted around the outer periphery of the third metal wire in the same manner. At this time, it is twisted around the third metal wire so that the two second metal wires 2a and 2b are twisted in opposite directions. The one second metal wire 2a and the other second metal wire 2b are combined so as to preferably cross with a constant pitch to manufacture a three-strand wire 5. Three of these three-strand wires 5 are manufactured.

At least two of the second metal wires 2a and 2b are twisted together on the outer peripheral surface of each of the third metal wires 3a-3c in a helical shape in opposite directions and preferably with a constant spacing. The locations where the second metal wires cross, namely, the crossing points of the second metal wires form projections 8. In the illustrated example, the projections 8 are arranged in a straight line with a constant spacing in the lengthwise direction of the third metal wire. Such linear arrangement of the projections 8 can also be seen on the rear side of the third metal wire.

The projections 8 and indentations 9 which extend in the lengthwise direction of the third metal wires 3a-3c are formed by the crossing points 8 of the two second metal wires 2a and 2b. At this time, the height from the indentations 9 to the projections 8 is two times the diameter of the second metal wires.

Then, as shown in FIG. 3, a wire saw body 6 is manufactured by winding at least one and preferably three three-strand wires 5 combining two second metal wires 2a and 2b on a first metal wire 1 in the same direction. At this time, at least the diameter of the third metal wires is added to the height of the projections 8, so the projections 8 become even farther from the outer peripheral surface of the first metal wire 1. The indentations 9 have bottoms corresponding to the outer peripheral surface of the first metal wire on their lower side thereof, so the space for removing chips formed by cutting is further increased. This situation is the same if the number of third metal wires which are wound is increased to two or three.

A wire saw body 6 which is manufactured in this manner is cut to a convenient length and then used as a wire saw 7. If necessary, loop-shaped engaging portions are provided at both ends of the cut wire saw body 6 to obtain a portable wire saw. A convenient installation fitting can also be provided at both ends of the wire saw body 6 when it is used for industrial purposes.

EXAMPLES

The present invention will be explained more specifically while referring to examples.

Figure 4:
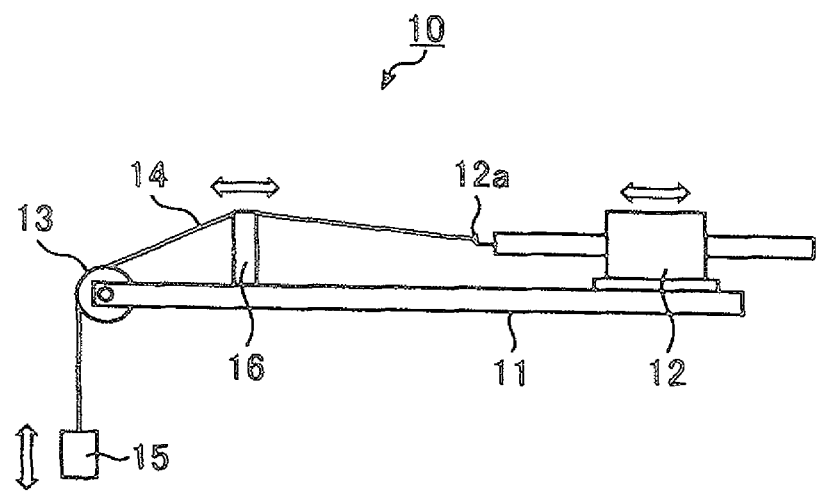
FIG. 4 is an explanatory view schematically showing the structure of a cutting test machine used in examples.
Figure 5:
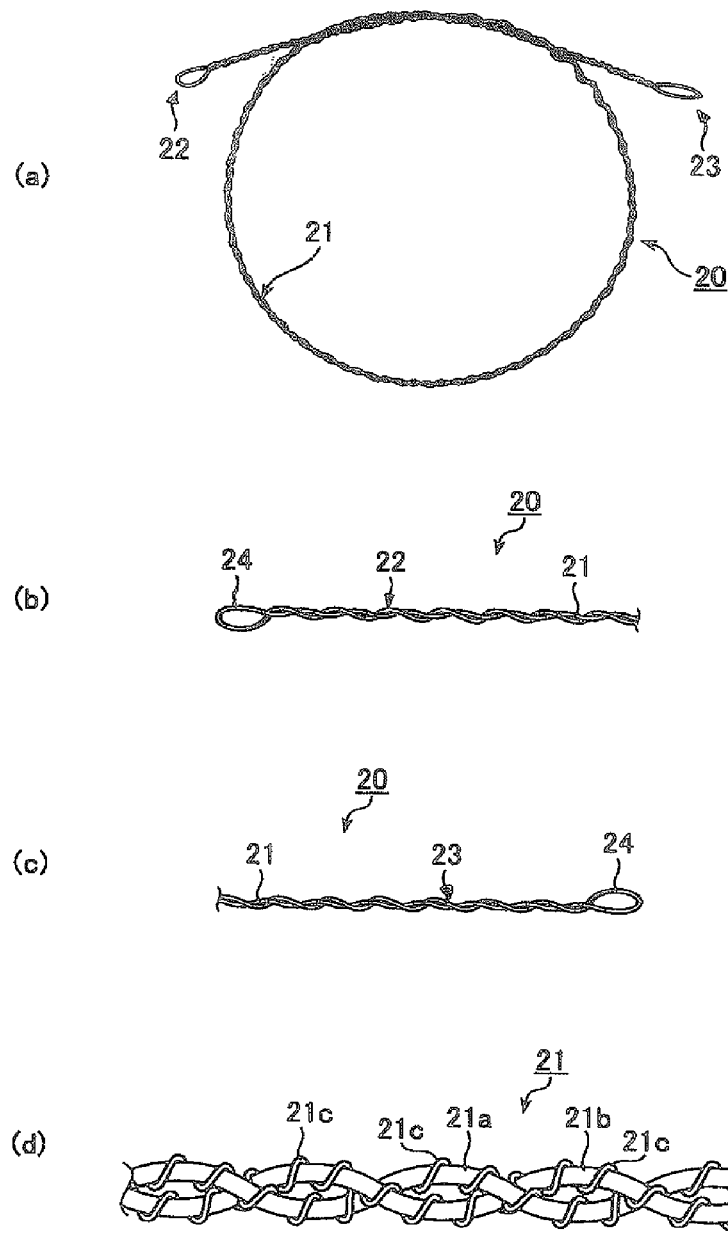
FIG. 5 comprises explanatory views showing a conventional wire saw in the form of a Gigli wire saw.

FIG. 4 is an explanatory view schematically showing the structure of a cutting test machine 10 used in examples.

As shown in FIG. 4, the cutting test machine 10 has a support base 11, a linear head 12, a pulley 13, a wire saw 14, and a three-kilogram weight 15. The linear head 12 reciprocates (strokes) atop the support base 11. The pulley 13 is disposed at the end of the support base 11. The wire saw 14 is engaged with a hook 12a at the end of the linear head 12 and passes over the pulley 13 and hangs down. The weight 15 is secured to the lower end of the wire saw 14. Thus, one end of the wire saw 14 is connected to the linear head 12, and the other end has the weight 15 hanging from it.

Examples of a wire saw 7 according to the present invention shown in FIG. 3 and a conventional example of a wire saw (product name: Gigli wire saw, product number COD-75-1018-04, length of 305 mm, manufactured and sold by Johnson & Johnson K.K.) were used as a wire saw 14.

The specifications of the wire saw 7 were as follows:

diameter and breaking load of first metal wire 1: 0.46 mm and 405.2 N, respectively diameter and breaking load of second metal wires 2a and 2b: 0.12 mm and 18.9 N, respectively, diameter and breaking load of third metal wires 3a-3c: 0.30 mm and 144.2 N, respectively, overall length of wire saw: 500 mm (same as the conventional example of a wire saw), helical period of second metal wires 2a and 2b: 1.0 mm in the lengthwise direction of the third metal wire 3, spacing of the third metal wires 3a-3c: 2.5 mm in the lengthwise direction of the first metal wire 1, and helical period of third metal wires 3a-3c: 7.0 mm in the lengthwise direction of the first metal wire 1.

Two types of material were used for the wire saw 7, namely, a cobalt-based alloy (Example 1: 20 mass percent of Cr, 15 mass percent of W, 10 mass percent of Ni, a remainder of Co and impurities) and stainless steel (Example 2: SUS316L austenitic stainless steel.)

The test piece being cut was a PVC plate 16 (thickness of 10 mm), which was disposed atop the support base 11 so as to contact the wire saw 14. Next, the linear head 12 was reciprocated atop the support base 11 in the direction of the arrow in the figure, and when it had moved back and forth a prescribed number of times (100, 300, 500, or 700 back and forth movements), the depth of cutting of the PVC plate 16 was measured.

The conditions for reciprocating movement of the linear head 12 were a stroke length of 200 mm and a stroke speed of 45 mm per second (4.4 seconds per back and forth movement) for 100 strokes. The depth of cutting of the PVC plate 16 was measured every 25 strokes. These conditions for reciprocating movement correspond to the conditions of reciprocating movement when a physician severs a limb of an injured person with a wire saw at the site of emergency medical treatment.

The test results are compiled in Table 1.

TABLE 1

| Category | Depth of groove (mm) | | | |
| --- | --- | --- | --- | --- |
| | 100 back and forth movements | 300 back and forth movements | 500 back and forth movements | 700 back and forth movements |
| Example 1 | 6.0 | 12.6 | 15.0 | 16.1 |
| Example 2 | 3.0 | 7.0 | 9.0 | 10.2 |
| Comparative Example | 2.3 | 6.1 | 7.4 | 8.5 |
| Ratio compared to conventional example | 1.3-2.6 | 1.2-2.1 | 1.2-2.1 | 1.2-1.9 |

As shown in Table 1, Examples 1 and 2 according to the present invention had 1.2-2.6 times the cutting ability of the conventional example over the entire range of 100-700 back and forth movements. Specifically, Example 1 according to the present invention had 1.9-2.6 times the cutting ability of the conventional example, and Example 2 according to the present invention had 1.2-1.3 times the cutting ability of the conventional example.

The surface of the wire saw was visually observed after 100 back and forth movements. The surface of the wire saw for Examples 1 and 2 according to the present invention was visible, and few chips formed by cutting remained. For the conventional example, only a small portion of the surface of the wire saw was visible due to remaining chips formed by cutting, and a large amount of chips remained. From this fact, it was ascertained that Examples 1 and 2 according to the present invention had better ability to remove chips formed by cutting than the conventional example.

The invention claimed is:

1. A wire saw comprising a body having a first wire and a multi-strand wire helically wound around an outer periphery of the first wire in a plurality of continuous complete turns, the multi-strand wire comprising a third wire and two second wires each helically and continuously wound around the third wire in opposite rotational directions from each other in a plurality of complete turns so that in each of the plurality of turns of the second wires, each of the second wires crosses and contacts the other second wire.

2. A wire saw as claimed in claim 1 wherein a diameter of the first wire is larger than a diameter of each of the second wires, and a diameter of the third wire is smaller than the diameter of the first wire and larger than the diameter of each of the second wires.

3. A wire saw as claimed in claim 1 wherein a breaking load of the first wire is larger than a breaking load of the third wire, and the breaking load of the third wire is larger than a breaking load of each of the second wires.

4. A wire saw as claimed in claim 1 wherein the first wire, the second wires, and the third wire are made of piano wire, a cobalt-based alloy, or stainless steel.

5. A wire saw as claimed in claim 1 including engaging portions provided on both ends of the body for engaging the body with a handle.

6. A method of manufacturing a wire saw as claimed in claim 1 comprising:

manufacturing at least one two-strand wire by winding one second wire on a third wire in a plurality of continuous complete turns;

manufacturing at least one three-strand wire by winding another second wire around each two-strand wire in the opposite rotational direction from the one second wire in a plurality of continuous complete turns so that in each of the plurality of turns of the second wires, each of the second wires crosses and contacts the other second wire; and winding each three-strand wire on a first wire in a plurality of continuous complete turns to obtain a wire saw as claimed in claim 1.

7. A method of amputating a human limb comprising cutting the limb with a wire saw as claimed in claim 1.

8. A wire saw as claimed in claim 1 wherein the first wire, the second wires, and the third wire are made of metal.

9. A wire saw as claimed in claim 1 wherein the second wires are helically wound around the third wire with the same pitch as each other.

10. A wire saw as claimed in claim 1 including a plurality of multi-strand wires helically wound around the first wire in a plurality of continuous complete turns in the same rotational direction as each other without crossing each other, each of the multi-strand wires comprising a third wire and two second wires helically wound around the third wire in opposite rotational directions from each other in a plurality of continuous complete turns so that in each of the plurality of turns of the second wires, each of the second wires crosses and contacts the other second wire.

11. A wire saw as claimed in claim 1 wherein the multi-strand wire contacts the outer periphery of the first wire.

12. A wire saw as claimed in claim 1 wherein the second wires contact an outer periphery of the third wire.

13. A method as claimed in claim 6 wherein the first, second, and third wires are made of metal.

14. A method as claimed in claim 6 wherein the second wires are wound around the third wire with the same pitch as each other.

15. A method of manufacturing a wire saw comprising:

preparing a multi-strand wire comprising a third wire and two second wires helically wound around the third wire, wherein preparing the multi-strand wire comprises helically winding one of the second wires around the third wire in contact with an outer periphery of the third wire and forming a plurality of continuous complete turns around the third wire, and helically winding the other second wire around the third wire in a plurality of continuous complete turns in the opposite rotational direction from the one second wire so that in each of the plurality of turns of the second wires, each of the second wires crosses and contacts the other second wire; and helically winding the multi-strand wire around a first wire with the multi-strand wire contacting an outer periphery of the first wire.

16. A method as claimed in claim 15 including preparing a plurality of multi-strand wires each comprising a third wire and two second wires helically wound around the third wire, wherein preparing each multi-strand wire comprises helically winding one of the second wires of the multi-strand wire around the third wire of the multi-strand wire in contact with an outer periphery of the third wire and forming a plurality of continuous complete turns around the third wire, and helically winding the other second wire of the multi-strand wire around the third wire in a plurality of continuous complete turns in the opposite rotational direction from the one second wire so that in each of the plurality of turns of the second wires, each of the second wires crosses and contacts the other second wire; and helically winding each multi-strand wire around the first wire in the same rotational direction as each other with each multi-strand wire contacting the outer periphery of the first wire.

\* \* \* \* \*